(12) United States Patent
Fuller et al.

(10) Patent No.: US 7,871,771 B2
(45) Date of Patent: *Jan. 18, 2011

(54) METHOD FOR NUCLEIC ACID ANALYSIS

(75) Inventors: Carl W. Fuller, Berkeley Heights, NJ (US); John R. Nelson, Clifton Park, NY (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 876 days.

This patent is subject to a terminal disclaimer.

(21) Appl. No.: 11/570,347

(22) PCT Filed: Jun. 9, 2005

(86) PCT No.: PCT/US2005/020378

§ 371 (c)(1), (2), (4) Date: Dec. 11, 2006

(87) PCT Pub. No.: WO2005/123957

PCT Pub. Date: Dec. 29, 2005

(65) Prior Publication Data

US 2008/0287305 A1  Nov. 20, 2008

Related U.S. Application Data

(60) Provisional application No. 60/578,789, filed on Jun. 10, 2004.

(51) Int. Cl.
 *C12Q 1/68* (2006.01)
 *C07H 21/02* (2006.01)
 *C07H 21/04* (2006.01)

(52) U.S. Cl. .......................... 435/6; 536/23.1; 536/24.3

(58) Field of Classification Search .................... 435/6; 536/23.1, 24.3

See application file for complete search history.

(56) References Cited

U.S. PATENT DOCUMENTS

| | | | |
|---|---|---|---|
| 6,274,320 B1* | 8/2001 | Rothberg et al. | 435/6 |
| 6,322,988 B1* | 11/2001 | Dawson et al. | 435/6 |
| 6,479,267 B1* | 11/2002 | Davis et al. | 435/194 |
| 6,828,100 B1* | 12/2004 | Ronaghi | 435/6 |
| 7,264,934 B2* | 9/2007 | Fuller | 435/6 |
| 2002/0164629 A1 | 11/2002 | Quake et al. | |
| 2003/0108867 A1 | 6/2003 | Chee et al. | |
| 2004/0033522 A1* | 2/2004 | Fischer | 435/6 |
| 2005/0100932 A1* | 5/2005 | Lapidus et al. | 435/6 |

OTHER PUBLICATIONS

Reha-Krantz, L., et al., "The proofreading pathway of bacteriophage T4 DNA Polymerase", Journal of Biological Chemistry, vol. 273, No. 36, Sep. 4, 1998, p. 22969-22976.

Kumar, J., et al., "Role of the C-terminal residue of the DNA polymerase of bacteriophage T7", Journal of Biological Chemistry, vol. 276, No. 37, Sep. 14, 2001, p. 24905-24912.

Doublie, S., et al., "An Open and Closed Case for all Polymerases", Structure, Feb. 1999, vol. 7, p. R31-R35.

* cited by examiner

*Primary Examiner*—Ethan Whisenant
(74) *Attorney, Agent, or Firm*—Yonggang Ji

(57) ABSTRACT

This invention provides methods for nucleic acid analysis. A closed complex of nucleic acid template, nucleotide and polymerase can be formed during polymerase reaction, absent divalent metal ion. This is used to trap the labeled nucleotide complementary to the next template nucleotide in the closed complex. Detection of the label allows determination of the identity of this next correct nucleotide. Identification can be either in place, as part of the complex, or as the dye is eluted from the complex when the reaction cycle is completed by the addition of divalent metal ion. In this way, sequential nucleotides of a DNA can be identified, effectively determining the DNA sequence. This method can be applied to nucleic acid single molecules or to collections of identical or nearly identical sequence such as PCR products or clones. Multiple templates can be sequenced in parallel, particularly if they are immobilized on a solid support.

26 Claims, 7 Drawing Sheets

Binding of next correct nucleotide by FY7 DNA polymerase forms a stable "closed" complex which can be isolated by non-denaturing PAGE

METHOD FOR NUCLEIC ACID ANALYSIS

CROSS REFERENCE TO RELATED APPLICATIONS

This application claims priority to U.S. patent application Ser. Nos. 10/772,996, 10/773,000, both filed Feb. 5, 2004; 10/651,362, 10/651,355, 10/651,582, 10/651,558, all filed Aug. 29, 2003; 10/358,818, filed Feb. 5, 2003; 10/113,030, 10/113,025, both filed Apr. 2, 2002; 10/230,576, filed Aug. 29, 2002; and U.S. provisional patent application Nos. 60/578,789, filed Jun. 10, 2004; the disclosures of which are incorporated herein by reference in their entirety.

FIELD OF THE INVENTION

The present invention relates generally to methods of sequencing a polynucleotide in a sample, based on the use of labeled nucleotides as substrates for nucleic acid polymerases.

BACKGROUND OF THE INVENTION

DNA polymerases are enzymes which are useful in many recombinant DNA techniques, such as nucleic acid amplification by the polymerase chain reaction ("PCR"), self-sustained sequence replication ("3 SR"), and DNA sequencing. Thermostable DNA polymerases are particularly useful. Because heat does not destroy the polymerase activity, there is no need to add additional polymerase after every denaturation step.

In its catalytic cycle, the DNA polymerase-DNA complexes formed are known to undergo a rate-limiting, conformational transition from an 'open' to 'closed' state, upon binding of the 'correct' dNTP or ddNTP at the active site. In the 'closed' state, $Mg^{2+}$ (or other metal ion) mediates a rapid chemical step involving nucleophilic displacement of pyrophosphate by the 3' hydroxyl of the primer terminus. The enzyme returns to the 'open' state upon the release of pyrophosphate (PPi) and translocation initiates the next round of reaction. While the ternary complex (Enzyme-DNA-dNTP (or ddNTP) can form in the absence of $Mg^{2+}$ (or other metal ions), it is proficient in chemical addition of nucleotide only in the presence of $Mg^{2+}$ (or other metal ions). $Mg^{2+}$ (or other metal ion)-deficient conditions tend to lead to non-covalent (physical) sequestration of first 'correct' dNTP in a tight ternary complex (Doublie et al. (15 Feb. 1999) *Structure Fold. Des.*, 7(2):R31-5).

SUMMARY OF THE INVENTION

This invention makes use of the above observation by use of this closed complex to freeze the polymerase during DNA synthesis, trapping the nucleotide which is complementary to the next template nucleotide, to allow the determination of the identity of this next correct nucleotide. It can then be identified either in place, as part of the complex, or as the dye is eluted from the complex when the reaction cycle is completed by the addition of divalent metal ion. In this way, sequential nucleotides of a DNA can be identified, effectively determining the DNA sequence. This method can be applied both to single molecules of template nucleic acid or to collections of identical (or nearly identical) sequence such as PCR products or clones. If desired, multiple templates can be sequenced in parallel, particularly if they are effectively immobilized on a solid Support such as plates or beads.

DEFINITIONS

Figure 1:
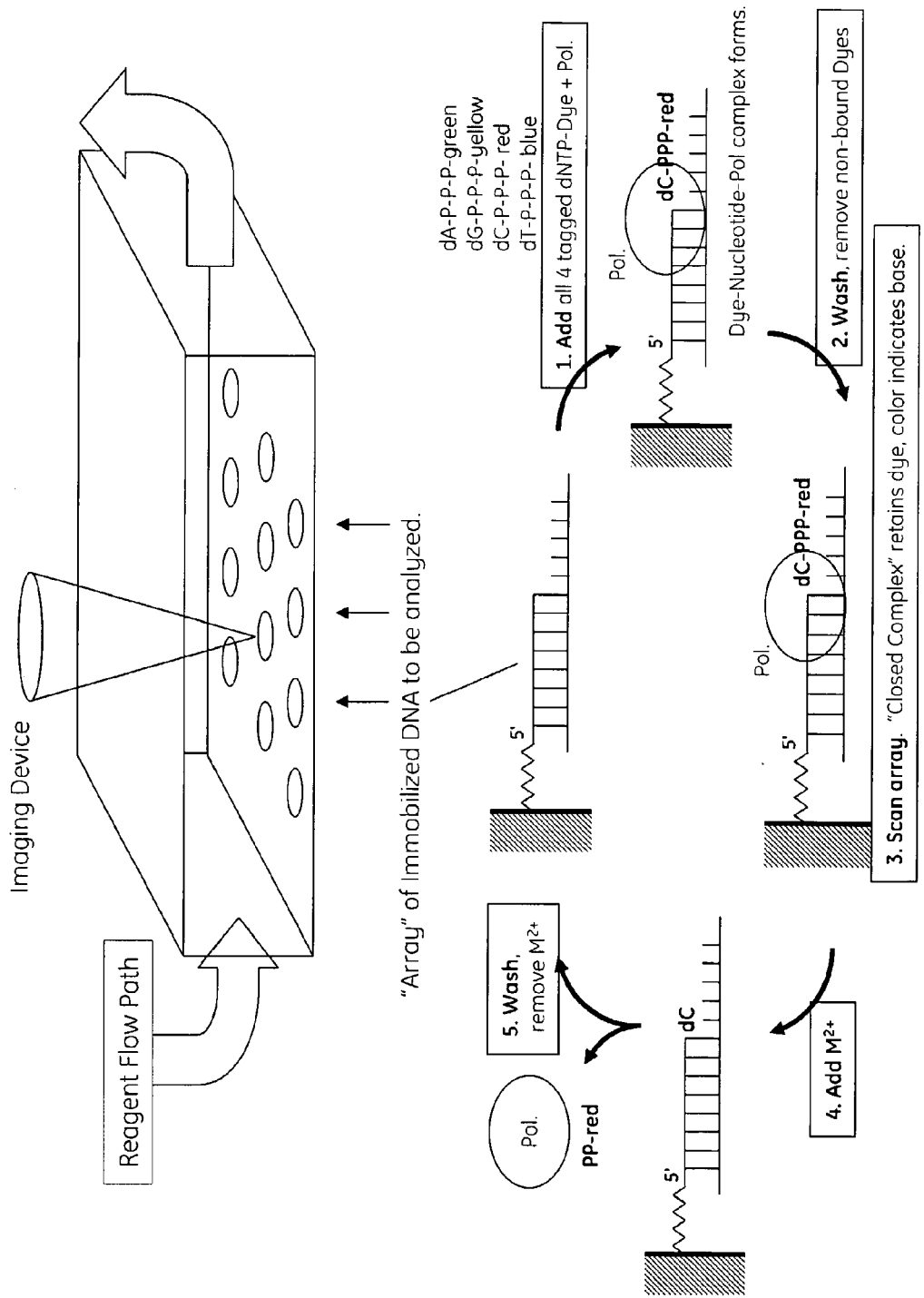
FIG. 1 depicts the reaction scheme for parallel sequencing by phosphate labeled nucleotides pausing at the closed complex stage of arrays of targets. Complex is stable for the full time scale of washing and scanning.

The term "nucleoside" as defined herein is a compound including a purine, deazapurine, pyrimidine or modified base linked to a sugar or a sugar substitute, such as a carbocyclic or acyclic moiety, at the 1' position or equivalent position and includes 2'-deoxy and 2'-hydroxyl, and 2', 3'-dideoxy forms as well as other substitutions.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid sequence and allows for amplification of that unique sequence.

The phrase "target nucleic acid sequence" and the like refers to a nucleic acid whose sequence identity, or ordering or location of nucleosides is determined by one or more of the methods of the present invention.

DETAILED DESCRIPTION OF THE PREFERRED EMBODIMENTS

The present invention relates to methods of characterizing a polynucleotide in a sample wherein a convenient assay is used for monitoring RNA or DNA synthesis via nucleic acid polymerase activity. Nucleic acid polymerizing enzymes synthesize nucleic acid molecules via transfer of a nucleoside monophosphate from a nucleoside triphosphate (NTP) or deoxynucleoside triphosphate (dNTP) to the 3' hydroxyl of a growing oligonucleotide chain. This reaction also releases inorganic pyrophosphate. During the catalytic cycle of the polymerase reaction, DNA polymerase-DNA complexes formed are known to undergo a rate-limiting, conformational transition from an 'open' to 'closed' state, after binding of the 'correct' dNTP or ddNTP at the active site. In the absence of $Mg^{2+}$ (or other divalent cations), the ternary complexes (Enzyme-DNA-dNTP (or ddNTP) form, but the dNTP or ddNTP is not added to the growing nucleic acid molecule. This leads to non-covalent (physical) sequestration of the next, 'correct' nucleotide in the ternary complex. This invention makes use of this observation by use of this closed complex to freeze the polymerase during nucleic acid synthesis, trapping the nucleotide which is complementary to the next template nucleotide, to allow the determination of the identity of this next correct nucleotide. In this way, the sequence of a DNA or RNA molecule can be built up one nucleotide at a time.

In certain embodiments, the polymerase is a DNA polymerase, such as DNA polymerase I, II, or III or DNA polymerase $\alpha$, $\beta$, $\gamma$, or terminal deoxynucleotidyl transferase or telomerase. In other embodiments, suitable polymerases include, but are not limited to, a DNA dependent RNA polymerase, a primase, or an RNA dependant DNA polymerase (reverse transcriptase). When RNA polymerase is used, a promoter sequence recognizable by the RNA polymerase is contained within the nucleic acid template or the primer sequence.

The nucleic acid template for sequencing in the methods of this invention may include an RNA or DNA template. When RNA is used as a template, the nucleic acid polymerizing enzyme can be a reverse transcriptase or an RNA polymerase.

The methods provided by this invention utilize a nucleoside polyphosphate, such as a deoxynucleoside polyphosphate, dideoxynucleoside polyphosphate, carbocyclic nucleoside polyphosphate, or acylic nucleoside polyphosphate analogue with a calorimetric dye, or a fluorescent label. The base in these nucleoside polyphosphate is selected from the group consisting of uracil, thymine, cytosine, 5-methylcytosine, guanine, 7-deazaguanine, hypoxanthine, 7-deazahypoxanthine, adenine, 7-deazaadenine, 2,6-diaminopurine and analogs thereof. To identify the bound nucleotide, the nucleotides are labeled with fluorescent dyes or colored dyes or other detectable tags. Suitable fluorescent dyes may be selected from the group consisting of a xanthene dye, a cyanine dye, a merrocyanine dye, an azo dye, a porphyrin dye, a coumarin dye, a bodipy dye and derivatives thereof. Suitable colored dyes may be selected from the group consisting of an azo dye, a merrocyanine, a cyanine dye, a xanthene dye, a porphyrin dye, a coumarin dye, a bodipy dye and derivatives thereof. These dyes are well known and are available from a number of commercial sources.

As described below, the methods of the current invention can be used to detect the sequence of a single molecule, or a homogeneous population of molecules. While the methods can be used to sequence unknown templates, it can also be used to confirm known sequences, identify single nucleotide polymorphisms, and perform single base extension reactions, amongst others. Cycling of the various steps of the methods leads to detection of additional sequence of the same molecule, one per cycle. When the aim is to sequence a single molecule, or a homogeneous population of molecules, the steps can be carried out in a sequential manner in a flow through or a stop-flow system. In such a flow through or stop flow system, the ternary complex of polymerase-template-nucleotide can be immobilized on beads, and the beads can be localized within a portion of a microchannel.

Alternatively, as described below, the methods of the current invention can also be adapted to perform massively parallel reactions, to sequence multiple templates at the same time. For multiplexed detections, the ternary complex of polymerase-template-nucleotide can be immobilized on beads within confined locations of a carrier (e.g. capillary), or they can be immobilized on the inner surface of a microchannel, or on a surface of a microscope slide or the like. The surface of a microscope slide can be a planar surface, or a coated surface. Additionally, the surface may comprise a plurality of microfeatures arranged in spatially discrete regions to produce a texture on the surface, wherein the textured surface provides an increase in surface area as compared to a non-textured surface.

The methods of the current invention require that the template-polymerase-nucleotide complex be immobilized to a support surface. It is contemplated that immobilization could occur before or after the formation of the ternary complex. When immobilization occurs before the formation of the ternary complex, one of several components could be immobilized. This includes the primer, the nucleic acid template, the nucleic acid polymerization enzyme, or the primer-template complex. When immobilization occurs after the formation of the ternary complex, the complex itself is immobilized. For multiplexed analysis of many sample templates, the species (the primer, the nucleic acid template, the nucleic acid polymerization enzyme, or the primer-template complex, or the ternary complex) immobilized can form an ordered pattern on the support surface. The species can also be immobilized randomly on the surface. However, each different species is located at a discrete location so that signal from any dye bound to one complex (or homogeneous population of complexes) is readily distinguishable from signal of another, adjacently immobilized complex.

The stability of the ternary complexes varies. As shown below, FY7 DNA polymerase (U.S. Pat. No. 6,479,267) can form a very stable complex with the template and dye-labeled nucleotide. In this case, step by step sequencing of a single molecule of nucleic acid using labeled dNTPs is possible. This method, when used in a multiplexed format, could allow sequencing of tens of thousands of templates simultaneously in a very short time or sequencing long regions of DNA. These methods are described in more detail below.

In one embodiment of the method of characterizing a target region of a nucleic acid template, the steps include: a) initiating a nucleic acid polymerization reaction on a support, by forming a reaction mixture, the reaction mixture including a nucleic acid template, a primer, a nucleic acid polymerizing enzyme, and four terminal-phosphate-labeled nucleotides each containing a distinct label, wherein a component of the reaction mixture or a first complex of two or more of the components, is immobilized on the support, and the component or components are selected from the group consisting of the nucleic acid template, primer, and nucleic acid polymerizing enzyme, and wherein each of the four terminal-phosphate-labeled nucleotides contains a base complementary to each of the four naturally occurring bases; b) progressing the nucleic acid polymerization reaction by incubating the reaction mixture to form a second complex comprising the nucleic acid template, primer, nucleic acid polymerizing enzyme, and a terminal-phosphate-labeled nucleotide, wherein the terminal-phosphate-labeled nucleotide contains a base complementary to the template base at the site of polymerization; c) removing unbound terminal-phosphate-labeled nucleotides and other components of the reaction mixture; d) detecting the label of the terminal-phosphate-labeled nucleotide from the second complex; and therefore identifying the nucleotide bound.

In this embodiment, the template used for the nucleic acid polymerase reaction is a single molecule, or a homogeneous population of molecules. For sequencing additional bases after the first base, in addition to steps (a) through (d) above, the following steps are performed: e) adding a divalent cation to complete the polymerization reaction (now in the absence of free nucleotide); f) removing the divalent cation and other end products from the polymerization reaction; and g) repeating steps (a) through (f) for determining additional nucleotides in sequence.

Optionally, an excess of a chelating agent (e.g. EDTA) can be added in any or all of steps (a) through (d) and in particular step (f) to sequester any residual divalent cation that might be present in the reaction mixture. It is contemplated that a chelating agent can be added to each of the methods disclosed in the current invention, for the same purpose, whenever there is a need. Addition of the chelating agent does not interfere with the formation of the ternary complex of template-polymerase-dNTP (or ddNTP). This is experimentally shown in the examples provided below. These chelating agents are removed with the addition of the divalent cation (e.g. manganese or magnesium), which enables the completion of the polymerase reaction cycle.

When the scheme of the above embodiment is used to characterize a nucleic acid sequence of a nucleic acid template, sometimes less than all four terminal-phosphate-labeled nucleotides can be used. For example, only two terminal-phosphate-labeled nucleotides are needed when characterizing a bi-allelic SNP of a sample template. Only a single terminal-phosphate-labeled nucleotide is needed when determining the presence of a particular nucleic acid sequence in a sample template.

These embodiments, when used in a multiplexed format, could allow sequencing of tens of thousands of templates simultaneously in a very short time or sequencing long regions of DNA. Therefore, in one embodiment for parallel characterization of a target region of a plurality of nucleic acid templates provided herein, the steps include: a) immobilizing a plurality of primers or nucleic acid templates on a support structure, wherein each primer or nucleic acid template contains a unique sequence and wherein each primer (or multiple copies of the same primer) or template is localized to an identifiable, discrete location on the support structure; b) initiating a plurality of nucleic acid polymerization reactions on the support structure, by forming a reaction mixture, the reaction mixture including the plurality of primers, the plurality of nucleic acid templates, a nucleic acid polymerizing enzyme, and at least one terminal-phosphate-labeled nucleotides each containing a distinct label, wherein each of the terminal-phosphate-labeled nucleotides contains a base complementary to each of the four naturally occurring bases; c) progressing the nucleic acid polymerization reactions by incubating the reaction mixture to form a plurality of complexes, each comprising one of the plurality of primers, one of the plurality of nucleic acid template, the nucleic acid polymerizing enzyme, and a terminal-phosphate-labeled nucleotide, wherein the terminal-phosphate-labeled nucleotide contains a base complementary to the template base at the site of polymerization; d) removing unbound terminal-phosphate-labeled nucleotides and other components of the reaction mixture; e) detecting, at each of the identifiable, discrete locations, the distinct label of the terminal-phosphate-labeled nucleotide from the complex. In addition, the detected results are optionally recorded to data storage media; and the results converted to one of the four nucleotide sequences.

In this method, each of the template (or primer) used for the nucleic acid polymerase reaction is a single molecule or a homogeneous population of molecules. For sequencing additional bases after the first base, in addition to steps (a) through (e) above, the following steps are performed: f) adding a divalent cation to complete the polymerization reactions; g) removing the divalent cation and other end products from the polymerization reactions; and h) repeating steps (a) through (g) for the characterization of each additional nucleotide of the plurality of nucleic acid templates. FIG. 1 depicts the multiplexing embodiment of the invention.

In another embodiment of the method of sequencing a target region of a nucleic acid template provided herein, the steps include: (a) initiating a nucleic acid polymerization reaction on a support, by forming a reaction mixture, the reaction mixture including a nucleic acid template, a primer, a nucleic acid polymerizing enzyme, and at least one terminal-phosphate-labeled nucleotides each containing a distinct label, wherein a component of the reaction mixture or a first complex of two or more of the components, is immobilized on the support, and the component or components are selected from the group consisting of the nucleic acid template, the primer, and the nucleic acid polymerizing enzyme, and wherein each of the at least one terminal-phosphate-labeled nucleotides contains a base complementary to the four naturally occurring bases; (b) progressing the nucleic acid polymerization reaction by incubating the reaction mixture to form a second complex comprising the nucleic acid template, primer, nucleic acid polymerizing enzyme, and a terminal-phosphate-labeled nucleotide, wherein the terminal-phosphate-labeled nucleotide contains a base complementary to the template base at the site of polymerization; (c) removing unbound terminal-phosphate-labeled nucleotides and other components of the reaction mixture; (d) adding a divalent cation to complete the polymerization reaction; (e) detecting the label of the terminal-phosphate-labeled nucleotide from the second complex; (f) identifying the nucleotide bound; (g) removing the divalent cation and other end products from the polymerization reaction; and (h) repeating steps a) through g) for determining each additional nucleotide in sequence. In this embodiment, the template used for the nucleic acid polymerase reaction is a single molecule, or a homogeneous population of molecules.

Figure 2:
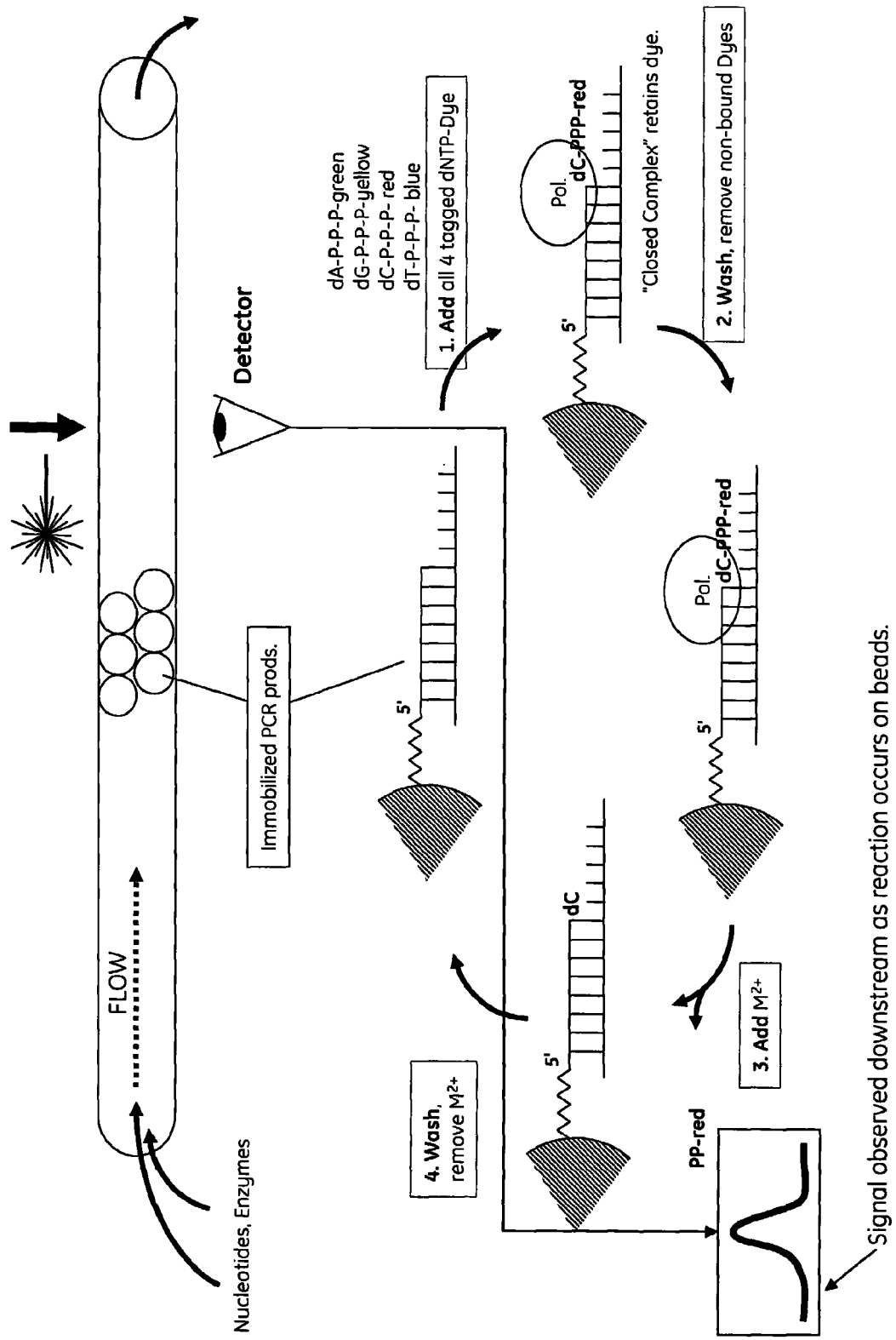
FIG. 2 depicts the reaction and detection scheme for sequencing by phosphate labeled nucleotides pausing at the closed complex stage. Complex is stable for the full time scale of washing and detection.

The present invention further provides methods of sequencing a target sequence using the steps described above in a continuous flow or a stop-flow system, where the immobilized material is held in place by any one of the means known in the art and different reagents and buffers are pumped in to the system at one end and exit the system at the other end. Reagents and buffers may flow continuously or may be held in place for certain time to allow for the polymerization reaction to proceed. An illustration of the process is presented in FIG. 2. As shown in FIG. 2, beads within a microchannel provide support surface for the immobilization of the reaction complexes. As the buffers and reagents move along through the system, the dye released from the polymerase reaction moves directionally toward the exiting end of the microchannel. Detection of the dye labeled dNTP (or ddNTP) captured by the polymerase can be performed at a number of locations within the system, even after the dye is released from the nucleotide by the addition of divalent cation. These locations include the one where the beads are held (before or after the additional of the divalent cation), or downstream of where the beads are held but before the dyes exit the system. Alternatively, the dye containing solution can be first collected as it exits the system, and then detected.

If the stability of the closed complex (which may be subject to reaction conditions such as pH or temperature) is such that it is only seconds instead of minutes, the method can still be used to sequence single molecules. The detection technique involves observing microscopic "flashes" of fluorescence at the site of the complex which would indicate the temporary (duration of seconds), binding of the next correct nucleotide (labeled), (resulting in a colored "glittering" of the DNA-DNA polymerase complex). Since the "closed complex" that is only formed with the next correct nucleotide, has at least 10-times longer lifetime than an open complex containing the incorrect next nucleotide, its fluorescence will dominate the observed signal at the site of the complex. This should be readily distinguishable from fluorescence of free nucleotide which will only remain at the site of the complex a very brief time, particularly when present at low concentration. While terminal phosphate labeled dNTPs or ddNTPs could be used, so could base labeled ddNTPs. The result is the identification of the single "next" nucleotide occurring at the 3' end of the primer. This information alone could be useful if primers are chosen to be adjacent to interesting loci such as SNPs.

These methods are described in more detail below. In one embodiment of the method of analyzing a target region of a nucleic acid template provided herein, the steps include: a) initiating a nucleic acid polymerization reaction on a support, by forming a reaction mixture, the reaction mixture including a nucleic acid template, a primer, a nucleic acid polymerizing enzyme, and at least one nucleotides each containing a distinct label, wherein a component of the reaction mixture or a first complex of two or more of the components, is immobilized on the support, and the component or components are selected from the group consisting of the nucleic acid template, the primer, and the nucleic acid polymerizing enzyme, and wherein one of the at least one labeled nucleotides contains a base complementary to the template base at the site of polymerization; b) incubating the reaction mixture to form a second complex comprising the nucleic acid template, primer, nucleic acid polymerizing enzyme, and one of the at least one labeled nucleotide, wherein the labeled nucleotide contains a base complementary to the template base at the site of polymerization, and wherein the labeled nucleotide is in dynamic equilibrium within the second complex; c) detecting the label of the labeled nucleotide; and d) identifying the nucleotide based on the detected distinctive label.

In this method, the template used for the nucleic acid polymerase reaction is a single molecule, or a homogeneous population of molecules. For analyzing additional bases after the first base, in addition to steps (a) through (d) above, the following steps are performed: e) removing the at least one labeled nucleotides and other components from the reaction mixture; f) adding, to the reaction mixture, a nucleic acid polymerizing enzyme, a divalent cation, and a nucleotide containing the base complementary to the template base at the site of polymerization; g) completing the polymerization reaction by incubating the reaction mixture for a period of time; h) removing the divalent cation, nucleotide and other end products from the polymerization reaction; and i) repeating steps (a) through (h) for each additional nucleotide to be analyzed.

The drawback to this method would be that runs of the same bases could not be fully sequenced. For example, a sequence of GGGTTTCCTCTC (SEQ ID NO: 1) would be read as GTCTCTC (SEQ ID NO: 2), but this information is useful in many situations, particularly when confirming known sequence.

These methods, when used in a multiplexed format, could allow sequencing of tens of thousands of templates simultaneously in a very short time or sequencing long regions of DNA. Therefore, in another embodiment for parallel characterization of a target region of a plurality of nucleic acid templates provided herein, the steps include: a) immobilizing a plurality of primers on a support structure, wherein each primer contains a unique sequence and wherein each primer (or multiple copies of each primer) is localized to an identifiable, discrete location on the support structure; b) initiating a plurality of nucleic acid polymerization reactions on the support structure, by forming a reaction mixture, the reaction mixture including the plurality of immobilized primers, a plurality of nucleic acid templates, a nucleic acid polymerizing enzyme, and four labeled nucleotides each containing a distinct label, wherein each of the four labeled nucleotides contains a base complementary to each of the four naturally occurring bases; c) incubating the reaction mixture to form a plurality of second complexes, each comprising one of the plurality of immobilized primers, one of the plurality of nucleic acid templates, the nucleic acid polymerizing enzyme, and a labeled nucleotide, wherein the labeled nucleotide contains a base complementary to the template base at the site of polymerization, and wherein said labeled nucleotide is in dynamic equilibrium within the second complex; d) detecting, at each of the identifiable, discrete locations, the label of the labeled nucleotide; e) recording data obtained from step d) to a data storage media; and f) characterizing the target sequence of each of the plurality of nucleic acid templates by converting the recorded data to one of the four nucleotides.

In this method, each of the template (or primer) used for the nucleic acid polymerase reaction is a single molecule or a homogeneous population of molecules. The drawback to this method would be that runs of the same bases could not be fully sequenced. For example, as stated above, a sequence of GGGTTTCCTCTC (SEQ ID NO: 1) would be read as GTCTCTC (SEQ ID NO: 2), but this information is useful in many situations. While this method only provides sequence information of the first base, cycling of a similar method can provide sequence information for multiple bases of each template.

Another method that could be used in a multiplexed format will also allow sequencing of tens of thousands of templates simultaneously in a very short time or sequencing long regions of DNA. This method could be used to obtain sequence of multiple bases from the same template, with the same limitation. Runs of the same bases could not be easily detected (e.g. GGGTTTCCTCTC (SEQ ID NO: 1)) would be read as GTCTCTC (SEQ ID NO: 2). Therefore, in another embodiment for parallel characterization of a target region of a plurality of nucleic acid templates provided herein, the steps include: a) immobilizing a plurality of primers on a support structure, wherein each primer contains a unique sequence and wherein each primer is localized to an identifiable, discrete location on the support structure; b) initiating a plurality of nucleic acid polymerization reactions on the support structure, by forming a reaction mixture, the reaction mixture including the plurality of immobilized primers, a plurality of nucleic acid templates, a nucleic acid polymerizing enzyme, and one labeled nucleotides; c) incubating the reaction mixture to form a plurality of second complexes, each comprising one of the plurality of immobilized primers, one of the plurality of nucleic acid templates, the nucleic acid polymerizing enzyme, and the labeled nucleotide, wherein the labeled nucleotide contains a base complementary to the template base at the site of polymerization, and wherein the labeled nucleotide is in dynamic equilibrium within the second complex; d) detecting, at the identifiable, discrete locations, the label of the labeled nucleotide; e) recording data obtained from the detecting step to a data storage media; f) removing labeled nucleotides and other components from the reaction mixture; g) adding, to the reaction mixture, a nucleic acid polymerizing enzyme, a divalent cation, and an un-labeled equivalent of the labeled nucleotide; h) completing the polymerization reaction by incubating the reaction mixture for a period of time; i) removing the divalent cation and other end products from the polymerization reaction; j) repeating steps a) through i) with one of the other three nucleotides, until all four nucleotides are tested; and k) repeating steps a) through j) for determining additional nucleotide sequences.

The data (dye label information) obtained from this method are processed in a computer system with an appropriate algorithm. The data are converted to sequence information of each of the four nucleotides, either instantaneously as the data is generated, or at the end of the experimental reactions. The sequences are next assembled for each of the plurality of nucleic acid templates. It is noted that the order of addition of labeled nucleotides can occur in a preset cycle, but it is not essential.

The following example illustrates the process for determining the sequence of two template nucleic acid molecules using the above method. Assuming the sequences to be analyzed are (a) GGGTTTCCTCTC (SEQ ID NO: 1) and (b) CTCTCCTTTTGGG (SEQ ID NO: 3) and nucleotides complementary to G, C, A, T, are added in this order. In the first of the cycle of step (j) above, a nucleotide complementary to G is added. A signal is detected from the location where the next nucleotide base on the template is a G (in this case SEQ ID NO: 1). A signal is not detected from the location where the next nucleotide base on the template is not a G (in this case SEQ ID NO: 3, which contains a next C). The information is recorded to a data storage media. In the second of the cycle, a nucleotide complementary to C is added. Now a signal is detected from the location that contains the template of SEQ ID NO: 3 (with a next C). A signal is not detected from the location that contains the template of SEQ ID NO: 1 (with a next T). Again, this information is recorded to a data storage media. As the cycles continue, data regarding the two templates are obtained. If a full cycle of reactions with each of the four nucleotides gives no detectable data, it signals that the template sequence is completely sequenced. The end result from the reactions, for the template of SEQ ID NO: 1, reads as GTCTCTC (SEQ ID NO: 2), while the end result from the reactions, for the template of SEQ ID NO: 3, reads as CTCTCTG (SEQ ID NO: 4).

If the stability of the closed complex is such that it can only be measured from seconds to a few minutes, the method can still be used to sequence single molecules. The detection technique involves observing microscopic "flashes" at the site of the complex which would indicate the temporary (duration of seconds to minutes), binding of the next correct nucleotide (labeled). While terminal phosphate labeled dNTPs or ddNTPs could be used, so could base labeled ddNTPs. The only drawback to this technique would be that runs of the same bases could not be fully sequenced. For example, a sequence of GGGTTTCCTCTC (SEQ ID NO: 1) would be read as GTCTCTC (SEQ ID NO: 2), but this information is useful.

These methods are described in more detail below. In one embodiment of the method of analyzing a target region of a nucleic acid template provided herein, the steps include: (a) initiating a nucleic acid polymerization reaction on a support, by forming a reaction mixture, the reaction mixture including a nucleic acid template, a primer, a nucleic acid polymerizing enzyme, and at least one nucleotides each containing a distinct label, wherein a component of the reaction mixture or a first complex of two or more of the components, is immobilized on the support, and the component or components are selected from the group consisting of the nucleic acid template, primer, and nucleic acid polymerizing enzyme, and wherein one of the at least one labeled nucleotides contains a base complementary to the template base at the site of polymerization; (b) incubating the reaction mixture to form a second complex comprising the nucleic acid template, primer, nucleic acid polymerizing enzyme, and one of the at least one labeled nucleotide, wherein the labeled nucleotide contains a base complementary to the template base at the site of polymerization, and wherein the labeled nucleotide is in dynamic equilibrium within the second complex; (c) removing, from the reaction mixture, un-bound portion of the at least one labeled nucleotides and other components of the reaction mixture; (d) detecting the label of the labeled nucleotide; and (e) identifying the nucleotide sequence based on the detected distinctive label.

In this method, the template used for the nucleic acid polymerase reaction is a single molecule, or a homogeneous population of molecules. For analyzing additional bases after the first base, in addition to steps (a) through (e) above, the following steps are performed: (f) adding, to the reaction mixture, a nucleic acid polymerizing enzyme, a divalent cation, and an un-labeled nucleotide containing identified base sequence; (g) completing the polymerization reaction by incubating the reaction mixture for a period of time; (h) removing the divalent cation and other end products from the polymerization reaction; and (i) repeating steps (a) through (h) for each additional nucleotide to be sequenced. If the labeled nucleotides are base labeled, it is preferred that an additional wash step is performed before step (f) to get rid of the template-primer-polymerase complex captured labeled nucleotides.

Figure 3:
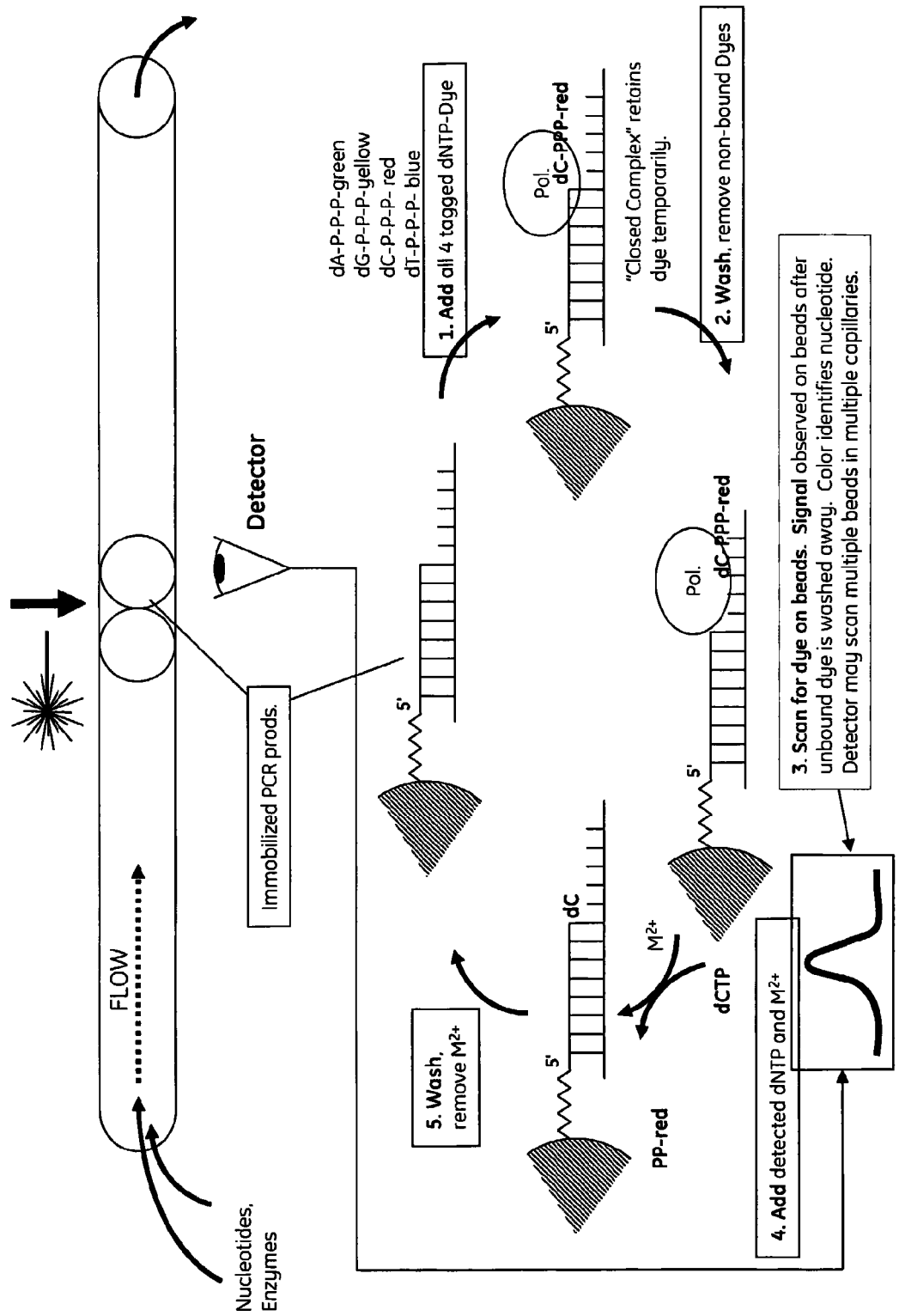
FIG. 3 depicts the reaction and detection scheme for sequencing by phosphate labeled nucleotides pausing at the closed complex stage. Complex is only partially stable for the full time scale of washing and detection. Sequence obtained will not distinguish multiples of a base (A, AA, AAA etc.) in the sequence.

FIG. 3 depicts the reaction and detection scheme for sequencing by phosphate labeled nucleotides pausing at the closed complex stage as detailed above. The only drawback of this method is that runs of the same bases could not be fully sequenced. For example, as stated above, a sequence of GGGTTTCCTCTC (SEQ ID NO: 1) would likely be read as GTCTCTC (SEQ ID NO: 2), but this information is useful in many situations.

These methods, when used in a multiplexed format, could allow sequencing of tens of thousands of templates simultaneously in a very short time or sequencing long regions of DNA. Therefore, in another embodiment for parallel characterization of a target region of a plurality of nucleic acid templates provided herein, the steps include: (a) immobilizing a plurality of primers on a support structure, wherein each primer contains a unique sequence and wherein each primer (or multiple copies of each primer) is localized to an identifiable, discrete location on the support structure; (b) initiating a plurality of nucleic acid polymerization reactions on the support structure, by forming a reaction mixture, the reaction mixture including the plurality of immobilized primers, a plurality of nucleic acid templates, a nucleic acid polymerizing enzyme, and four labeled nucleotides each containing a distinct label, wherein each of the four labeled nucleotides contains a base complementary to each of the four naturally occurring bases; (c) incubating the reaction mixture to form a plurality of second complexes, each comprising one of the plurality of immobilized primers, one of the plurality of nucleic acid templates, the nucleic acid polymerizing enzyme, and a labeled nucleotide, and the labeled nucleotide contains a base complementary to the template base at the site of polymerization, and the labeled nucleotide is in dynamic equilibrium within the second complex; (d) removing, from the reaction mixture, un-bound labeled nucleotides and other components of the reaction mixture; (e) detecting, at each of the identifiable, discrete locations, the label of the labeled nucleotide; (f) recording information obtained about the label to a data storage media; and (g) characterizing the target nucleotide sequence of each of the plurality of nucleic acid templates by converting the recorded data to one of four nucleotides.

Figure 4:
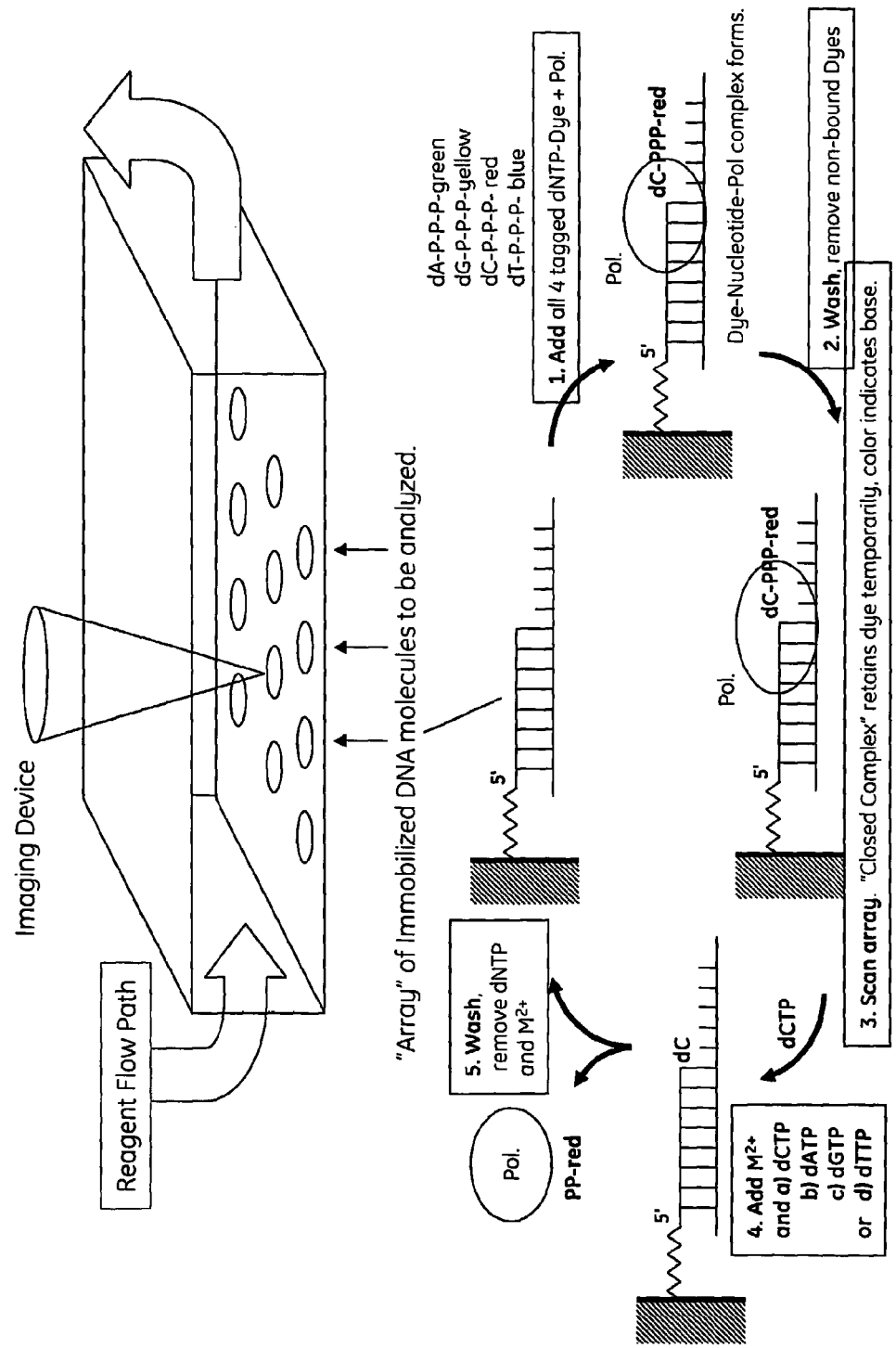
FIG. 4 depicts the reaction scheme for parallel sequencing by phosphate labeled nucleotides pausing at the closed complex stage of arrays of targets. Complex is only partially stable for the full time scale of washing and detection. Sequence obtained will not distinguish multiples of a base (A, AA, AAA etc.) in the sequence.

In this method, each of the template (or primer) used for the nucleic acid polymerase reaction is a single molecule or a homogeneous population of molecules. FIG. 4 depicts the reaction scheme for parallel sequencing as detailed hereinabove. The drawback to this method would be that runs of the same bases could not be fully sequenced. For example, as stated above, a sequence of GGGTTTCCTCTC (SEQ ID NO: 1) would be read as GTCTCTC (SEQ ID NO: 2), but this information is useful in many situations. While this method only provides sequence information of the first base, cycling of a similar method can provide sequence information for multiple bases of each template.

Another method that could be used in a multiplexed format will also allow sequencing of tens of thousands of templates simultaneously in a very short time or sequencing long regions of DNA. This method could be used to obtain sequence of multiple bases from the same template. Therefore, in another embodiment for parallel characterization of a target region of a plurality of nucleic acid templates provided herein, the steps include: (a) immobilizing a plurality of primers on a support structure, wherein each primer contains a unique sequence and wherein each primer is localized to an identifiable, discrete location on the support structure; (b) initiating a plurality of nucleic acid polymerization reactions on the support structure, by forming a reaction mixture, including the plurality of immobilized primers, a plurality of nucleic acid templates, a nucleic acid polymerizing enzyme, and at least one labeled nucleotides; (c) incubating the reaction mixture to form a plurality of second complexes, each comprising one of the plurality of immobilized primers, one of the plurality of nucleic acid templates, the nucleic acid polymerizing enzyme, and one of the at least one labeled nucleotide, each of the labeled nucleotide contains a base complementary to the template base at the site of polymerization, and the labeled nucleotide is in dynamic equilibrium within the second complex; (d) removing, from the reaction mixture, unbound labeled nucleotides and other components of the reaction mixture; (e) detecting, at the identifiable, discrete locations, the label of the labeled nucleotide; (f) recording data obtained from the detecting step to a data storage media; (g) adding, to the reaction mixture, a nucleic acid polymerizing enzyme, a divalent cation, and an un-labeled equivalent of the labeled nucleotide; (h) completing the polymerization reaction by incubating the reaction mixture for a period of time; (i) removing the divalent cation and other end products from the polymerization reaction; (j) repeating steps a) through i) with one of the other three nucleotides, until all four nucleotides are tested; and (k) repeating steps a) through j) for determining additional nucleotide sequences. If the labeled nucleotides are base labeled, it is preferred that an additional wash step is performed before step (g) to get rid of the template-primer-polymerase complex captured labeled nucleotides.

The data (dye label information) obtained from this method are processed in a computer system with an appropriate algorithm. The data are converted to sequence of each of the four nucleotides, either instantaneously as the data is generated, or at the end of the experimental reactions. The sequences are next assembled for each of the plurality of nucleic acid templates. It is noted that the order of addition of labeled nucleotides can occur in a preset cycle, but it is not essential.

EXAMPLES

The following examples present certain preferred embodiments of the instant invention but are not intended to be illustrative of all embodiments. These examples should not be construed as limiting the appended claims and/or the scope of this invention.

Example 1

Demonstration of the Formation of the "Closed Complex"

Figure 5:
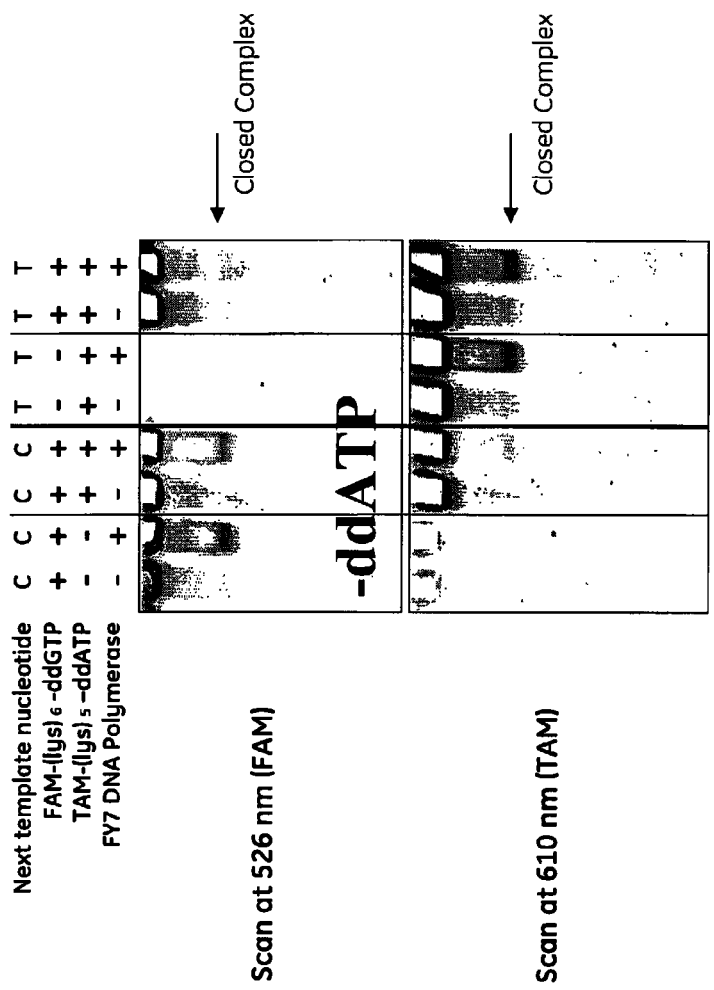
FIG. 5 presents evidence of the formation of the stable closed complex using fluorescently labeled nucleotides. It clearly demonstrates that the complex can be detected as described herein.

FIG. 5 presents evidence of the formation of this type of stable closed complex using fluorescently labeled nucleotides. It clearly demonstrates that the complex can be detected as described herein. Polymerase reactions (20 ul) were performed in (25 mM Tris:Borate, pH=7.5, 0.1 mM EDTA, 10% glycerol) and contained: 50 pmoles of primed template as indicated, +/−20 pmoles of labeled, positively charged ddGTP and/or ddATP; +/−3 pmoles FY7 DNA polymerase. Reaction products were separated on 7% PAGE in 50 mM Tris:Borate, pH=7.5. Complex formation is only observed when polymerase, primer template, and the correct nucleotide are present.

Figure 6:
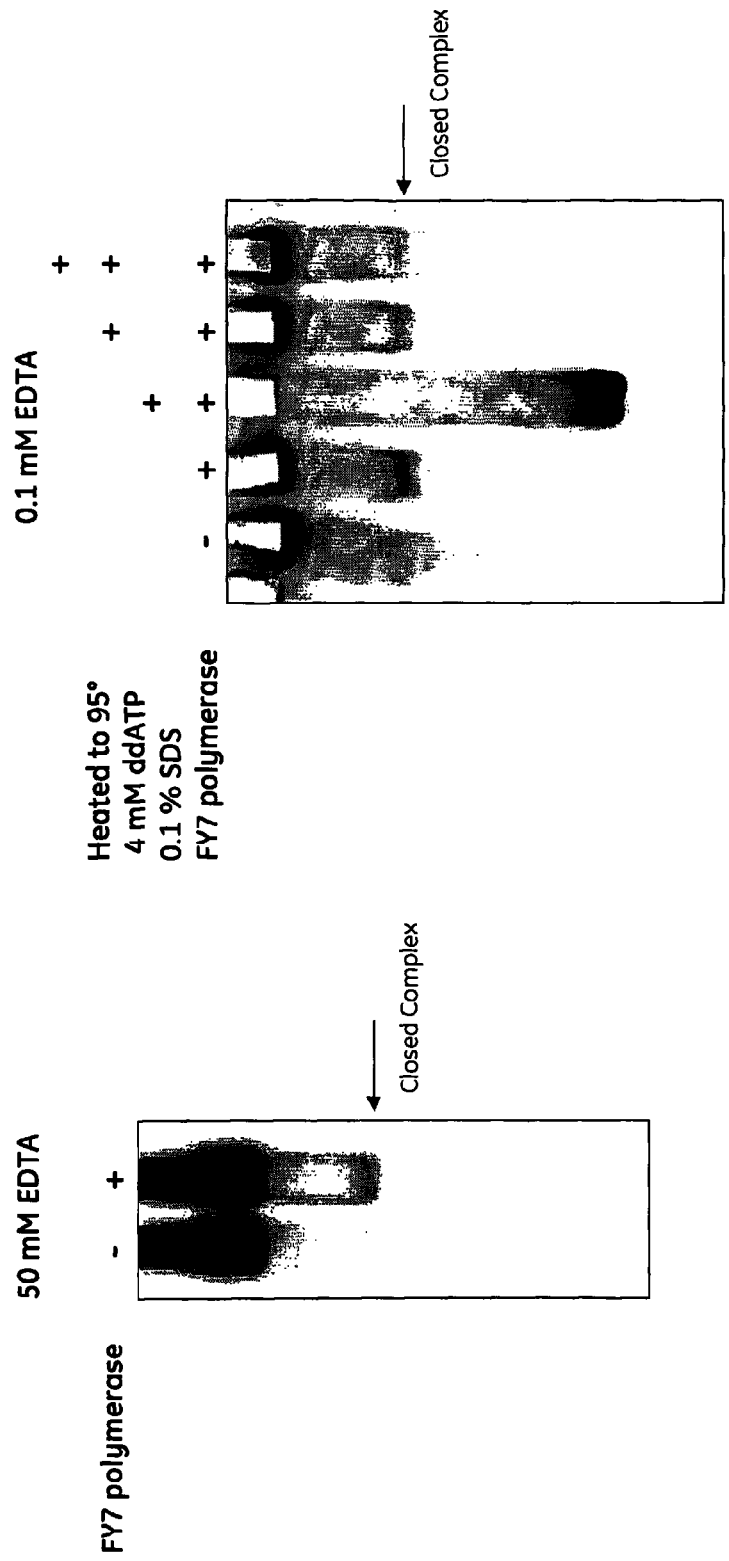
FIG. 6 demonstrates how SDS destroys the closed complex.

FIG. 6 demonstrates that the "closed complex" can be formed in up to 50 mM EDTA, can be destroyed with SDS, and competed with "cold" competitor. Reactions (20 ul) were performed in (25 mM Tris:Borate, pH=7.5, 50 or 0.1 mM EDTA as indicated on the Figure, and 10% glycerol) and contained: 50 pmoles of primed template with T as next template nucleotide, 20 pmoles of labeled, positively charged ddATP (next correct nucleotide), +/−3 pmoles FY7 DNA polymerase as indicated. After the complex was allowed to form, [4 mM ddATP]$_f$ was added as indicated on the Figure and the sample was heated to 95° for 30 seconds and allowed to cool before loading as indicated on the Figure. Reaction products were loaded and separated on a 7% PAGE in 50 mM Tris:Borate, pH=7.5. Closed complex of ddATP-template-FY7 DNA polymerase can be formed under 50 mM of EDTA and 0.1 mM of EDTA. Closed complex is destroyed, however, at the presence of 0.1% of SDS, and is competed with un-labeled "cold" ddATP.

Figure 7:
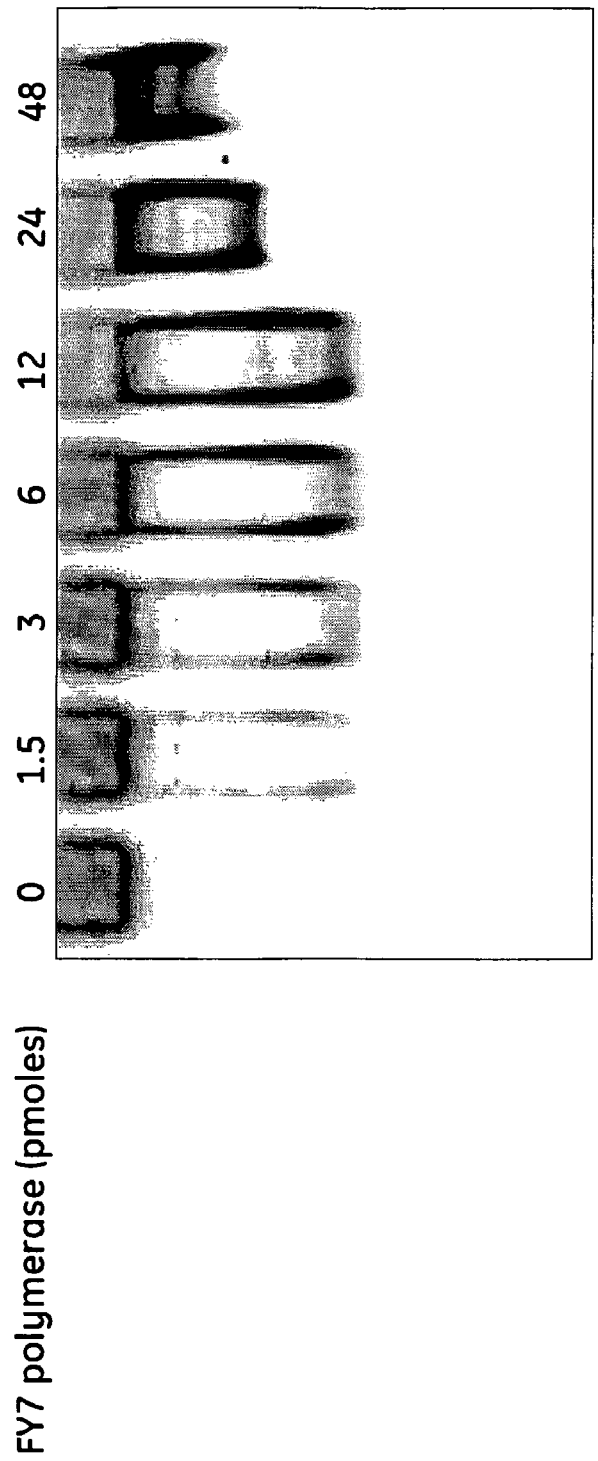
FIG. 7 demonstrates polymerase titration of the closed complex.

FIG. 7 demonstrates polymerase titration of the closed complex. Reactions (20 ul) were performed in (25 mM Tris:Borate, pH=7.5, 5 mM EDTA, 10% glycerol) and contained: 20 pmoles of primed template with T as next template nucleotide, 10 pmoles of labeled, positively charged ddATP (next correct nucleotide), and FY7 DNA polymerase as indicated. Reaction products were separated using 7% PAGE in 50 mM Tris:Borate, pH=7.5. Binding of next correct nucleotide by FY7 DNA polymerase forms a stable "closed complex" which can be isolated by non-denaturing PAGE. A close to linear increase of closed complex formation is observed with the increase of FY7 DNA polymerase.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method of characterizing a target region of a nucleic acid template, comprising:

a) initiating a nucleic acid polymerization reaction on a support, by forming a reaction mixture, said reaction mixture including said nucleic acid template, a primer, a nucleic acid polymerizing enzyme, and at least one terminal-phosphate-labeled nucleotides each containing a distinct label, wherein a component of said reaction mixture or a first complex of two or more of said components, is immobilized on said support, and said component or components are selected from the group consisting of said nucleic acid template, said primer, and said nucleic acid polymerizing enzyme, and wherein each of said at least one terminal-phosphate-labeled nucleotides contains a base complementary to each of the four naturally occurring bases;

b) progressing said nucleic acid polymerization reaction by incubating said reaction mixture, in the absence of a divalent cation, to form a second complex comprising said nucleic acid template, said primer, said nucleic acid polymerizing enzyme, and a terminal-phosphate-labeled nucleotide, wherein said terminal-phosphate-labeled nucleotide contains a base complementary to the template base at the site of polymerization;

c) removing unbound terminal-phosphate-labeled nucleotides and other components of said reaction mixture; and d) detecting the label of said terminal-phosphate-labeled nucleotide from said second complex to characterize said target region of said nucleic acid template.

2. The method of characterizing a target region of a nucleic acid template of claim 1, further comprising:

e) adding a divalent cation to complete said polymerization reaction;

f) removing said divalent cation and other end products from said polymerization reaction; and g) repeating steps a) through f) for determining each additional nucleotide sequence.

3. The method of claim 1 or 2, wherein said steps are carried out in a sequential manner in a flow through or a stop-flow system.

4. The method of claim 1 or 2, wherein said support is in the form of beads.

5. A method for parallel characterization of a target region of a plurality of nucleic acid templates, comprising:
   a) immobilizing a plurality of primers or nucleic acid templates on a support structure, wherein each primer or template contains a unique sequence and wherein multiple copies of each primer or template are localized to an identifiable, discrete location on said support structure;
   b) initiating a plurality of nucleic acid polymerization reactions on said support structure, by forming a reaction mixture, said reaction mixture including said plurality of primers, said plurality of nucleic acid templates, a nucleic acid polymerizing enzyme, and at least one terminal-phosphate-labeled nucleotides each containing a distinct label, wherein each of said at least one terminal-phosphate-labeled nucleotides contains a base complementary to each of the four naturally occurring bases;
   c) progressing said nucleic acid polymerization reactions by incubating said reaction mixture, in the absence of a divalent cation, to form a plurality of complexes, each comprising one of said plurality of primers, one of said plurality of nucleic acid template, said nucleic acid polymerizing enzyme, and a terminal-phosphate-labeled nucleotide, wherein said terminal-phosphate-labeled nucleotide contains a base complementary to the template base at the site of polymerization;
   d) removing unbound terminal-phosphate-labeled nucleotides and other components of said reaction mixture;
   e) detecting, at each of said identifiable, discrete locations, the distinct label of said terminal-phosphate-labeled nucleotide from said complex;
   f) recording data obtained from step e) to a data storage media; and
   g) characterizing said target region sequence of each of said plurality of nucleic acid templates by converting said data to one of said four nucleotides.

6. The method for parallel characterization of a target region of a plurality of nucleic acid templates of claim 5, further comprising:
   h) adding a divalent cation to complete said polymerization reactions;
   i) removing said divalent cation and other end products from said polymerization reactions; and
   j) repeating steps a) through i) for the characterization of each additional nucleotide of said plurality of nucleic acid templates.

7. The method of claim 5 wherein said support structure is beads, and wherein said beads carry one primer is identifiably separated from said beads carrying a different primer.

8. The method of claim 1 or 5 wherein said support structure is a first surface of a microscope slide.

9. The method of claim 1 or 5 wherein said labels in said terminal-phosphate-labeled nucleotides are fluorescent dyes or colored dyes.

10. The method of claim 1 or 5, wherein said nucleic acid polymerizing enzyme is FY7 DNA polymerase.

11. The claim of claim 1 or 5, wherein said nucleic acid polymerizing enzyme is selected from DNA polymerase, RNA polymerase, reverse transcriptase, a terminal nucleotidyl transferase, a primase, or a telomerase.

12. The method of claim 1 or 5, wherein said nucleic acid polymerizing enzyme is selected from DNA polymerase I, T4 DNA polymerase, Amplitaq FS, T7 DNA polymerase, Phi 29 DNA polymerase, Klenow exo⁻, Sequenase, Taq DNA polymerase, Thermo Sequenase I, ThermoSequenase II, FY7 DNA polymerase, ThemoSequenase E681M, *T. hypogea* (Thy B), *T. neapolitana* (Tne), *T. subterranea* (Tsu), *T. barossii* (Tba), *T. litoralis* (NEB Vent), *T. kodakaraensis* (Novagen), *P. furiosis* (Strategene), P. GB-D (NEB Deep Vent), Human Pol beta, Tsp JS1, AMV-reverse transcriptase, MMLV-reverse transcriptase and HIV-reverse transcriptase, or exonuclease deficient variants of these polymerases.

13. The method of claim 1 or 5, wherein said reaction mixture in said initiating step further includes EDTA.

14. The method of claim 2 or 6, wherein said divalent cation is magnesium.

15. The method of claim 2 or 6, wherein said divalent cation is manganese.

16. The method of claim 1, further comprising:
   prior to said detecting step d), adding a divalent cation to complete said polymerization reaction.

17. The method of sequencing a target region of a nucleic acid template of claim 16, further comprising:
   f) removing said divalent cation and other end products from said polymerization reaction; and
   g) repeating steps a) through f) for determining each additional nucleotide sequence.

18. A method of analyzing a target region of a nucleic acid template, comprising:
   a) initiating a nucleic acid polymerization reaction on a support, by forming a reaction mixture, said reaction mixture including a nucleic acid template, a primer, a nucleic acid polymerizing enzyme, and one to four nucleotides each containing a distinct label, wherein a component of said reaction mixture or a first complex of two or more of said components, is immobilized on said support, and said component or components are selected from the group consisting of said nucleic acid template, said primer, and said nucleic acid polymerizing enzyme, and wherein one of said one to four labeled nucleotides contains a base complementary to the template base at the site of polymerization;
   b) incubating said reaction mixture, in the absence of a divalent cation, to form a second complex comprising said nucleic acid template, said primer, said nucleic acid polymerizing enzyme, and one of said at least one labeled nucleotide, wherein said labeled nucleotide contains a base complementary to the template base at the site of polymerization, and wherein said labeled nucleotide is in dynamic equilibrium within said second complex;
   c) detecting said label of said labeled nucleotide; and
   d) identifying the sequence based on the detected distinctive label.

19. The method of analyzing a target region of a nucleic acid template of claim 18, further comprising:
   e) removing, from said reaction mixture, said at least one labeled nucleotides and other unbounded components of said reaction mixture;
   f) adding, to said reaction mixture, a nucleic acid polymerizing enzyme, a divalent cation, and a nucleotide containing the base complementary to the template base at the site of polymerization;
   g) completing said polymerization reaction by incubating said reaction mixture for a period of time;
   h) removing said divalent cation and other end products from said polymerization reaction; and
   i) repeating steps a) through h) for each additional nucleotide to be sequenced.

20. A method for parallel analysis of a plurality of nucleic acid templates, comprising:
   a) immobilizing a plurality of primers on a support structure, wherein each primer contains a unique sequence and wherein multiple copies of each primer are localized to an identifiable, discrete location on said support structure;

b) initiating a plurality of nucleic acid polymerization reactions on said support structure, by forming a reaction mixture, said reaction mixture including said plurality of immobilized primers, a plurality of nucleic acid templates, a nucleic acid polymerizing enzyme, and four labeled nucleotides each containing a distinct label, wherein each of said four labeled nucleotides contains a base complementary to each of the four naturally occurring bases;

c) incubating said reaction mixture, in the absence of a divalent cation, to form a plurality of second complexes, each comprising one of said plurality of immobilized primers, one of said plurality of nucleic acid templates, said nucleic acid polymerizing enzyme, and a labeled nucleotide, wherein said labeled nucleotide contains a base complementary to the template base at the site of polymerization, and wherein said labeled nucleotide is in dynamic equilibrium within said second complex;

d) detecting, at each of said identifiable, discrete locations, said label of said labeled nucleotide;

e) recording data obtained from step d) to a data storage media; and f) characterizing said target sequence of each of said plurality of nucleic acid templates by converting said recorded data to one of said four nucleotides.

21. A method for parallel analysis of a plurality of nucleic acid templates, comprising:

a) immobilizing a plurality of primers on a support structure, wherein each primer contains a unique sequence and wherein each primer is localized to an identifiable, discrete location on said support structure;

b) initiating a plurality of nucleic acid polymerization reactions on said support structure, by forming a reaction mixture, said reaction mixture including said plurality of immobilized primers, a plurality of nucleic acid templates, a nucleic acid polymerizing enzyme, and one labeled nucleotide;

c) incubating said reaction mixture, in the absence of a divalent cation, to form a plurality of second complexes, each comprising one of said plurality of immobilized primers, one of said plurality of nucleic acid templates, said nucleic acid polymerizing enzyme, and said labeled nucleotide, wherein said labeled nucleotide contains a base complementary to the template base at the site of polymerization, and wherein said labeled nucleotide is in dynamic equilibrium within said second complex;

d) detecting, at said identifiable, discrete locations, said label of said labeled nucleotide;

e) recording data obtained from said detecting step to a data storage media;

f) removing, from said reaction mixture, said labeled nucleotides and other components of said reaction mixture;

g) adding, to said reaction mixture, a nucleic acid polymerizing enzyme, a divalent cation, and an un-labeled equivalent of said labeled nucleotide;

h) completing said polymerization reaction by incubating said reaction mixture for a period of time;

i) removing said divalent cation and other end products from said polymerization reaction;

j) repeating steps a) through i) with one of the other three nucleotides, until all four nucleotides are tested; and k) repeating steps a) through j) for determining additional nucleotide sequences.

22. The method of claim 21, further comprising the step of:

l) characterizing said target sequences of said plurality of nucleic acid templates by converting said recorded data to sequence of one of said four nucleotides and assembling said target sequence for each of said plurality of nucleic acid templates.

23. The method of claim 18, further comprising:

prior to said detecting step c), removing, from said reaction mixture, said at least one labeled nucleotides and other unbound components of said reaction mixture.

24. The method of claim 20, further comprising:

prior to said detecting step d), removing, from said reaction mixture, said labeled nucleotides and other components of said reaction mixture.

25. The method of claim 21, wherein the order of addition of labeled nucleotides occurs in a preset cycle.

26. The method of claim 21, wherein said first removing step f) is performed prior to said detecting step d).

* * * * *

SEQUENCE LISTING

<160> NUMBER OF SEQ ID NOS: 4

<210> SEQ ID NO 1
<211> LENGTH: 12
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 1
gggtttcctc tc                                                          12

<210> SEQ ID NO 2
<211> LENGTH: 7
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 2 gtctctc                                                                 7

<210> SEQ ID NO 3
<211> LENGTH: 13
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 3
ctctcctttt ggg                                                         13

<210> SEQ ID NO 4
<211> LENGTH: 7
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 4 ctctctg                                                                 7